United States Patent [19]

Blair

[11] Patent Number: 4,895,165
[45] Date of Patent: Jan. 23, 1990

[54] ELECTRONIC ESTRUS DETECTOR

[76] Inventor: William D. Blair, 1000 Lakeshore Dr. #68, Brandon, Miss. 39042

[21] Appl. No.: 263,271

[22] Filed: Oct. 27, 1988

Related U.S. Application Data

[63] Continuation-in-part of Ser. No. 103,647, Oct. 2, 1987, abandoned.

[51] Int. Cl.[4] .............................................. A61B 10/00
[52] U.S. Cl. .................................... 128/738; 128/774; 119/1
[58] Field of Search ............... 128/738, 774, 775, 903; 340/573; 119/1

[56] References Cited

U.S. PATENT DOCUMENTS

| 3,076,431 | 2/1963 | Rule et al. | 235/92 |
| 4,247,758 | 1/1981 | Rodrian | 235/92 |
| 4,411,274 | 10/1983 | Wright | 128/903 |
| 4,635,587 | 1/1987 | Leonardo | 119/1 |

OTHER PUBLICATIONS

Thompson et al., "Transducers for Capture of Activity Data," *Journal of Dairy Science Supplement*, vol. 66 (Jun. 1983), pp. 115-126.
Foote, "Estrus Detection and Estrus Detection-Aids," *Dept. of Animal Science*, Cornell U. (Jul. 22, 1974), p. 248.
Williamson, "Improving Heat Detection," Dairy Herd Mat. (Jun. 1983).
Hurnik et al., "Estrous and Related Behaviour in Postpartum Holstein Cows." (May 1975).

*Primary Examiner*—Max Hindenburg
*Assistant Examiner*—Randy Citrin
*Attorney, Agent, or Firm*—Bacon & Thomas

[57] ABSTRACT

An electronic estrus detector that may be affixed to the back of a cow comprises a tapeswitch connected to a counter for storage and display of number of mounts by another cow. When a cow mounts another cow equipped with the estrus detector, the impact of the mounting cow upon the monitored cow closes the tapeswitch and increments the counter, such that the contents of the counter indicate the estrus condition of the monitored cow.

In a second embodiment, a modified electronic estrus detector indicates estrus condition based upon satisfaction of a mount-second index. A user programs the estrus detector to show when a specified number of mounts, coupled with a specified total time duration of all mounts, has occured.

13 Claims, 4 Drawing Sheets

ELECTRONIC ESTRUS DETECTOR

This application is a continuation-in-part of application Ser. No. 07/103,647, filed Oct. 2, 1987, now abandoned.

BACKGROUND OF THE INVENTION

1. Field of the Invention

The present invention relates generally to a device for detecting estrus in an animal. The invention relates more particularly to a device affixed to the back of a cow for recording mounting activity an an indicator of estrus in the mounted cow.

2. Description of the Related Art

Reproduction inefficiency among diary farm animals results in an estimated annular loss of hundreds of millions of dollars. Undetected estrus is a primary source of this loss, causing increase of calving interval, fewer calves born, lowered lifetime milk production, and wasted semen.

Several ideas for detecting estrus in cows are currently in use, including trained dogs that detect a characteristic odor; pedometers to measure increased activity; probes to measure electrical conductivity of cervical mucus; and sensors to measure both body and milk temperature. Nevertheless, the most widespread scheme used today is daily visual observation augmented by some type of heat detection patch, both of which are based on mounting activity.

When a cow is in heat (estrus), she will stand and allow another cow to mount her. Cows not in heat will not permit such homosexual behavior. Since standing for mounting is directly related to condition of estrus, a mount recording device that operates in the absence of constant observation would allow a dairy farmer to pinpoint estrus in his cows while freeing him to carry out his normal routine.

SUMMARY OF THE INVENTION

The present invention comprises a detector that may be affixed to the back of a cow such that, when another cow mounts the monitored cow, mounting activity may be recorded as an indicator of estrus in the monitored cow.

Although the detector could be partially or entirely mechanical, it is preferably a battery-operated electronic detector.

The detector preferably rests within a protective pouch that is adhesively attached to the back of a cow near its tailhead. The weight of the mounting cow on the detector activates a tapeswitch or other sensor, thereby incrementing a counter. The total count is selectively displayed either through a window in the pouch, or remotely via a display device into which the detector may be read upon removal from the pouch.

In a second embodiment of the present invention, a modified detector provides an output display that flashes to show estrus condition as a function of both total number of mounts and the sum of total times elapsed during each sensed mount taken together. According to this embodiment, estrus condition will not be indicated unless both conditions are met. A user programs circuitry to respond to a desired total sum of mount times, as well as to a desired total number of mounts. The user also programs indicating means to display a desired threshold representative of a logical function known as a mount-second index (MSI), which is a function of summed times and summed mounts. The indicating means also indicates the time elapsed since the first satisfaction of the user-programmed MSI.

By utilizing this second embodiment, the cow owner is provided an estrus indication of higher quality than that afforded by the first embodiment. An observer attempting to visually determine whether a cow is in estrus can easily tell not only how many times the cow has been mounted, but also whether the individual mounts are "quality" mounts, or simply chin rubbing or transient rubbing that would be considered normal in the course of the activity of a herd. The second embodiment provides the cow owner with information that he previously would have been able to obtain only by direct visual observation. Furthermore, because the ultimate indication of estrus is dependent upon both summed times and summed mounts, a small number of long-term mounts or a large number of short-term mounts, which might otherwise falsely indicate estrus condition where only one factor considered, will not provide an indication of estrus. Only where both a specified number of mounts of a total specified duration simultaneously exists will estrus be indicated.

DETAILED DESCRIPTION OF THE PREFERRED EMBODIMENTS

Figure 1A:
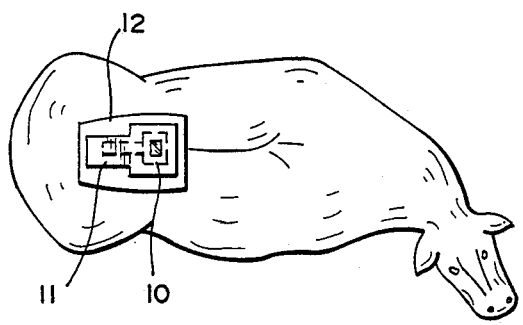
FIG. 1a is a plan schematic view of the detector attached to a cow.
Figure 1B:
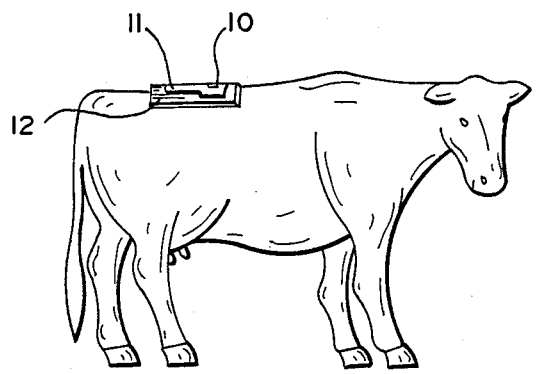
FIG. 1b is a side schematic view of the detector attached to a cow.

As shown in FIGS. 1a and 1b, estrus detector 10 is positioned along the backbone of a monitored cow near its tailhead. Detector 10 preferably rests within protective pouch 11, which may be made from nylon, canvas, fabric, or other similar materials or combinations of such materials. In the preferred form of the invention, pouch 11 is provided with a window that allows the detector display 4 to be selectively viewed without requiring removal of detector 10 from pouch 11. Pouch 11 is shown secured to the back of the cow by adhesive patch 12, although straps or other securing means may also be employed.

Figure 2:
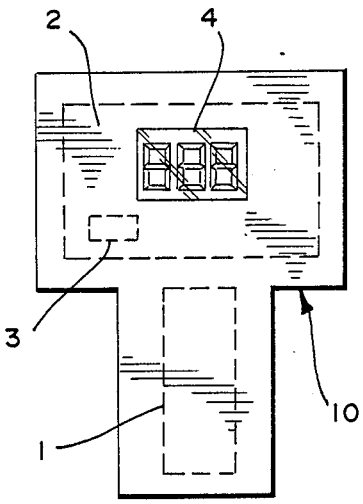
FIG. 2 illustrates a detector embodying the invention.

FIG. 2 shows a more detailed view of detector 10. Input sensor 1, shown in its preferred form as a tapeswitch, comprises the stem of a T-shaped detector device. Tapeswitch 1 is connected via appropriate circuitry, set forth more fully below with respect to FIGS. 3 and 4, to counting and storage electronics shown generally as processing unit 2. Processing unit 2 is hermetically sealed within the epoxy-encapsulated housing of detector 10, and thus is protected against shock and weather hazards. Reset switch 3 is also hermetically sealed within the housing, and comprises a simple reed switch, actuable by a magnet (not shown) to reset both a counter within processing unit 2 and display 4. The entire system is preferably powered by a 3V battery sealed within the housing.

Figure 3:
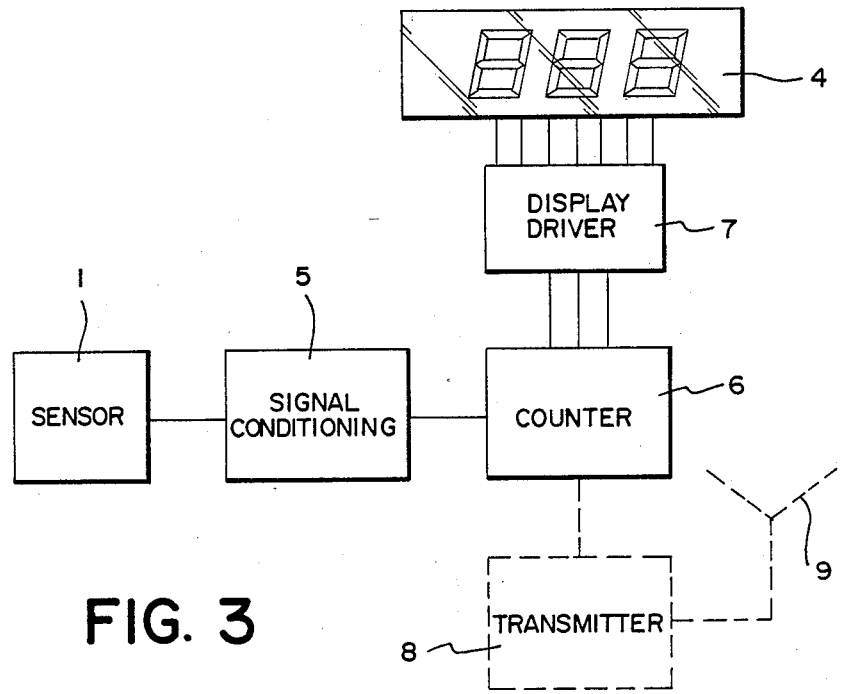
FIG. 3 shows a block diagram of the detector circuitry.

Selective display 4 is represented by a three-digit liquid crystal display, designed to show the current total cow mountings (i.e., since the counter was last reset). The use of a liquid crystal display is arbitrary and merely representative of an operative display mode for the system. Alternatively, a light-emitting diode display may be substituted by employing simple changes to the circuitry. Detector 10 may also be provided with an output port to allow its count to be displayed via any conventional remote display means. Specifically, detector 10 may be designed to deliver its output via a radio frequency link to a remote receiver, or it may provide an electrical connector for accession by a remote display. FIG. 3 illustrates in dotted lines the radio-frequency link embodiment, wherein conventional transmitter 8 and antenna 9 are employed.

Figure 4:
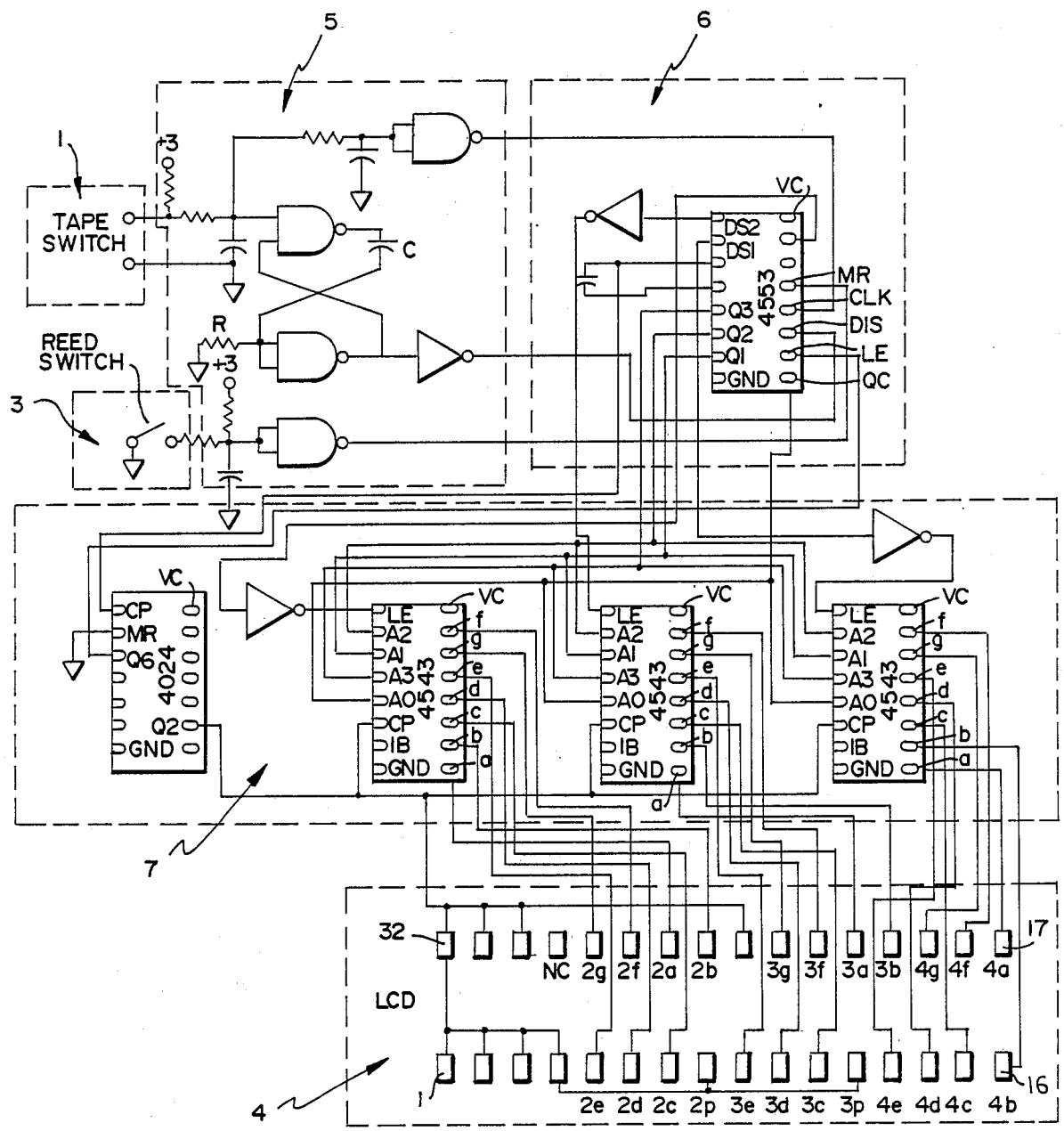
FIG. 4 shows a detailed schematic of the detector circuitry.

FIGS. 3 and 4 illustrate, respectively, a block diagram and detailed schematic of the counting and storage electronics that comprise processing unit 2. Each closing of tapeswitch 1 (i.e., caused by mounting activity), shown generically as a sensor in FIG. 3, sends an input signal via signal conditioner 5 to counter 6. Signal conditioner 5 debounces the input signal and prevents the recording of any tapeswitch closure signal of duration less than, e.g. 3.0 seconds. In this manner, false "mounts" such as chin rubbing, tail switching, and other incidental contact causing tapeswitch closure will not be recorded. Minimum tapeswitch closure time required for count incrementation is determined by the charging time of capacitor C through resistor R, both of which may be varied to tailor the minimum closure time to the needs of the cow owner.

Counter 6, in preferred form, comprises a conventional three-digit binary coded decimal (BCD) counter. Counter 6 stores and provides the current total of recorded mounts at its outputs. Counter 6 further controls display control 7 by selecting the individual display driver integrated circuit chips for incrementation upon proper activation of the input sensor. Display control 7 can then activate selective display 4 to show total mounts and, thus, the estrus condition of the monitored cow.

Figure 5:
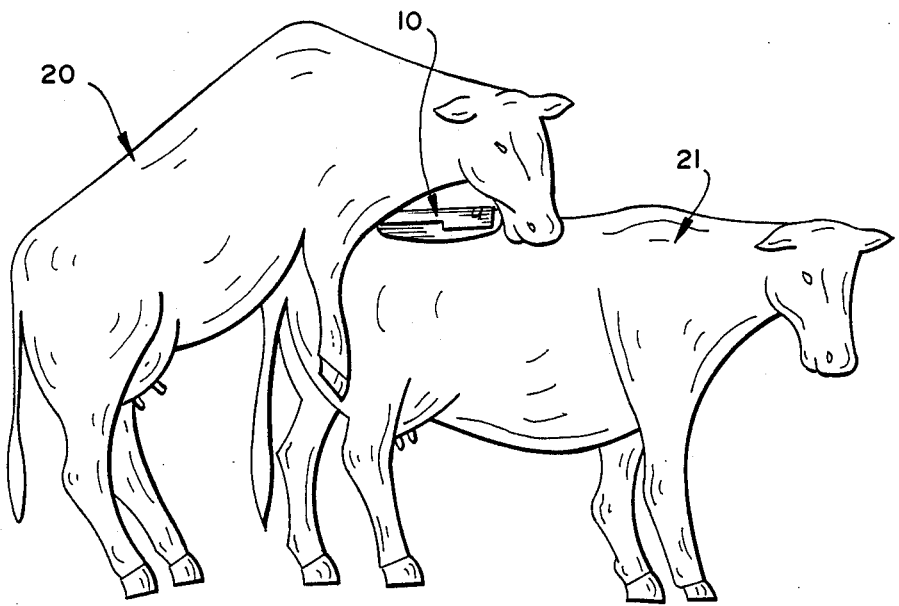
FIG. 5 shows the detector in use as it is actuated by a mounting cow.

FIG. 5 shows the detector 10 in use in its preferred mode of operation. Mounting cow 20, in assuming the position shown, actuates tapeswitch 1, which therefore records a mount in storage device 7. Tapeswitch 1 is shown in place along the backbone of mounted cow 21 and beneath mounting cow 20; the detector electronics may be located proximal to the tapeswitch or further from the impact area to protect the electronics, and thus connected by two signal wires to the tapeswitch. As described above, the input sensor is preferably a tapeswitch; however, another appropriate sensor, including a heat sensor, load sensor, or any other proximity or impact detector, may be employed.

Figure 6:
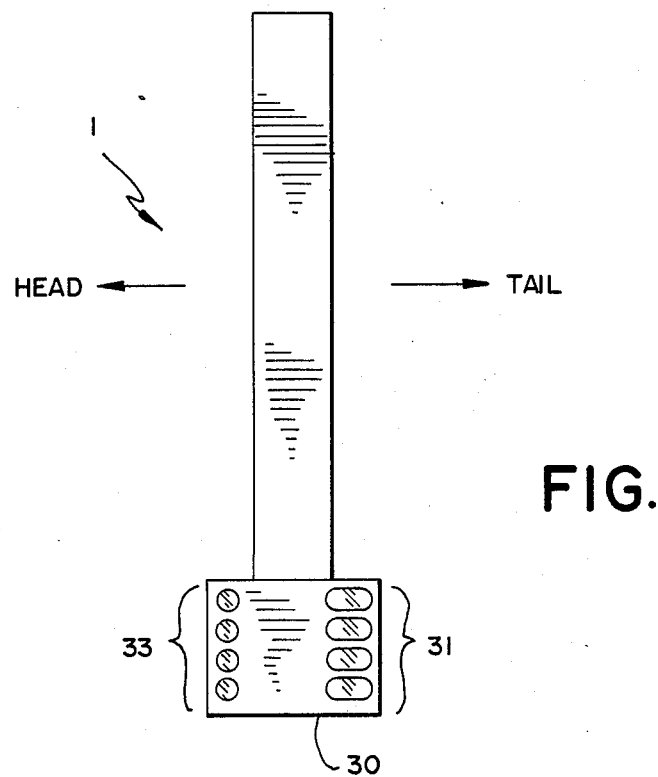
FIG. 6 shows an estrus detector constructed according to a second embodiment of the present invention.

FIG. 6 shows a second embodiment of an estrus detector constructed in accordance with the present invention. Indicating means 30, which is preferably a liquid crystal display, provides an indication of estrus based upon both the total number of mounts and the sum of all times elapsed during all sensed mounts. In preferred form, indicating means 30 is designed to flash with bright color upon satisfaction of a user-programmed mount-second index (MSI), a function based upon these two mount conditions. The currently programmed MSI is displayed on indicating means 30, as shown generally at 31. The indicating means also preferably displays, generally at 33, an indication of elapsed time since the first such indication.

Figure 7:
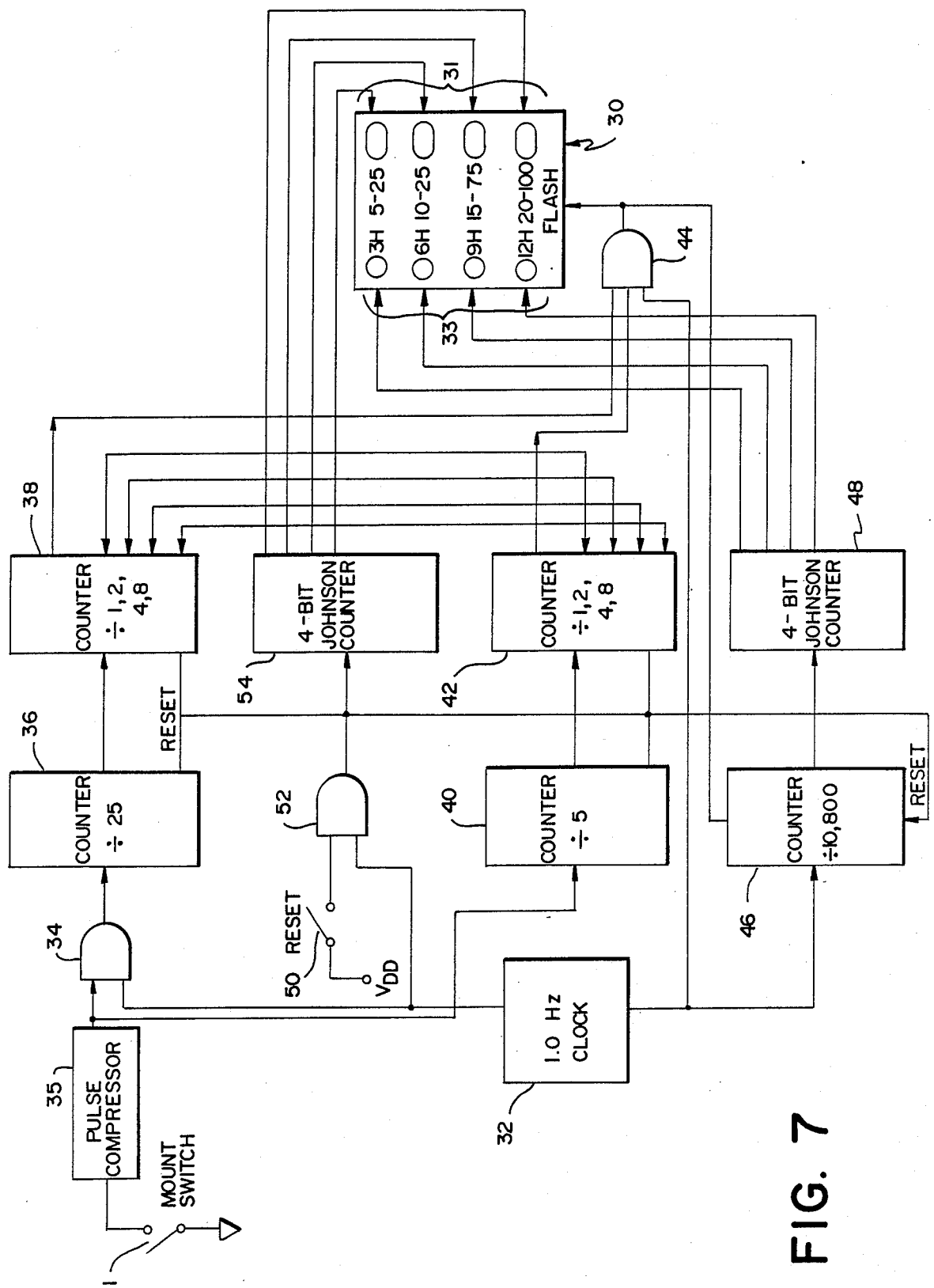
FIG. 7 shows a detailed schematic of the detector circuitry incorporated into the second embodiment.

With reference also to FIG. 7, each sensed mount (i.e., a mount that satisfies a threshold time) contributes both to a sum of mount times and to a sum of mounts. Clock 32, which is preferably a 1.0 Hz clock, outputs pulses to one input of dual input AND gate 34. The other input of AND gate 34 comes from mount switch 1, via pulse compressor 35, which corresponds to the input signal conditioner of the first embodiment. The output of AND gate 34, therefore, alternates between logical 1 and logical 0 for as long as pulse compressor 35 outputs a signal. Counter 36 is a divide-by-25 counter that outputs a pulse every 25 seconds of summed mount times. A mount time, thus, is the total time elapsed for a single closure of mount switch 1, that satisfies a threshold closure time. For example, if a first mount results in closure of switch 1 for a time period of 5 seconds, AND gate 34 will "output" two logical 1 pulses (5 seconds of mount time minus a nominal three-second threshold level) to counter 36. If a second mount results in closure of switch 1 for a time period of eight seconds, AND gate 34 will pulse the input of counter 36 five more times, or a total of seven. When counter 36 has been pulsed a total of twenty-five times at its input, it will output a pulse to counter 38. Counter 38 is shown as a divide-by-one, -two, -four or -eight counter, and is preferably a divide-by-two counter. In this manner, a total of fifty seconds of mount times will be required for counter 38 to output a pulse.

The output taken from pulse compressor 35 is also provided to counter 40, which is a divide-by-five counter. Counter 40 operates similarly to counters 36 and 38 in that five sensed mounts are required before counter 40 will output a pulse. Counter 42, like counter 38, may be either a divide-by-one, -two, -four or -eight counter. It also is preferably a divide-by-two counter, so that it will output a pulse for each ten sensed mounts.

The outputs of counters 38 and 42 are provided to the two inputs of AND gate 44. AND gate 44 will output a pulse to the SET input of flip-flop 45 whenever both the desired sum of mounted times and a desired total mounts conditions are satisfied. The Q output of flip-flop 45 provides one input of AND gate 47, whose other input is provided by clock 32. The output of AND gate 47 is delivered simultaneously to the FLASH of indicating means 30 and to the incrementing input of counter 46.

Counter 46 is provided to implement another feature of this second embodiment. Indicating means 30 is arranged to indicate additionally the total time elapsed from initial satisfaction of the MSI. As shown in FIG. 7, indicating means 30 includes, illustratively at 33, four locations representing four elapsed time periods. When the MSI is satisfied and AND gate 47 outputs a logical 1, counter 46 begins to increment at a rate dictated by clock 32. At the same time, indicating means 30 flashes at the same rate. Counter 46 is preferably a divide-by-10,800 counter, although the count ratio may be changed depending upon the time interval desired by the operator to be displayed. For every 10,800 clock pulses, counter 46 outputs a pulse to four-bit Johnson counter 48. Counter 48, which is essentially a ring counter, outputs a logical 1 sequentially along its four outputs for every input pulse from counter 46. In this manner, one location on indicating means 30 displays a time interval elapsed for each input to counter 48. For example, where counter 46 is a divide-by-10,800 counter and clock 32 is a 1.0 Hz clock, counter 46 will output a pulse every three hours to counter 48, which will thus energize a different location in indicating means 30 every three hours. As shown in FIG. 7, the four locations represent three-hour, six-hour, nine-hour and twelve-hour intervals. Should the operator desire a more precise indication of elapsed time, either clock 32 or counter 46 may be altered to so provide. Counter 48 and indicating means 30 may also require modification should the operator require greater than four time intervals to be shown.

In order to provide greater flexibility for use of the present invention, and to give the operator greater discretion in its use, counters 38 and 42 are preferably variable. Indicating means 30 is thus provided with means for indicating the MSI, programmed by the operator according to his desire for number of mounts and summed mount times. A reset switch 50, which may be similar to reset switch 3 of the first embodiment, provides both a means for indicating the programmed MSI at 31 as well as for programming the MSI. When the operator desires to change the MSI, he merely activates reset switch 50, which provides an input to dual input AND gate 52. The second input of AND gate 52 is provided by clock 32, which allows alternating logical 1 and 0 signals to appear at the output of AND gate 52 periodically while switch 50 is closed. These alternating pulses increment four-bit Johnson counter 54, which varies the divide-by settings of counters 38 and 42, and also changes the MSI indication of indicating means 30. The output of AND gate 52 may also be tied to the resets of flip-flop 45 and counters 36, 38, 40, 42, 46 and 48 as shown to allows automatic reset of the entire detector when the MSI is adjusted. Alternatively, a separate reset switch (not shown) may be employed to accomplish this objective.

While indicating means 30 has been described above in a specific manner, one of ordinary skill in the art could customize it to fit many requirements. Indicating means 30 could be expanded to include other indications, or certain of the indications described above could be eliminated. For example, should the user not desire an indication of time elapsed from first satisfaction of MSI, such indication could be deleted. This and similar modifications may require minor alterations in the circuit and indicating means. As such, indicating means 30 is a custom device, but is relatively easily manufactured and modified using known techniques.

A person of ordinary skill in the art will recognize that the estrus detector disclosed above is not limited to use with cows, but may function equally well for a variety of animals whose mating habits resemble those of bovines.

While specific embodiments of the invention have been illustrated and described above, it is realized that numerous modifications and changes will occur to one skilled in the art. It is therefore to be understood that the appended claims are intended to cover all such modifications and changes as fall within the true spirit and scope of the invention.

I claim:

1. An estrus detector for detecting estrus in animals that manifest onset of estrus by standing for estrus mounting activity by another animal, comprising:

means for sensing estrus mounts including means for generating estrus mount signals;
   means for processing said estrus mount signals, including:
   means for numerically summing and storing sensed estrus mounts;
   means for programming a desired sum of sensed estrus mounts;
   means for detecting and storing the approximate time elapsed during a sensed estrus mount as an estrus mount time;
   means for summing the estrus mount times for all sensed estrus mounts;
   means for programming a desired sum of all estrus mount times;
   means for determining that a first condition has been satisfied, wherein said first condition is that the sum of sensed estrus mounts is at least equal to the desired sum of sensed estrus mounts;
   means for determining that a second condition has been satisfied, wherein said second condition is that the sum of all estrus mount times is at least equal to the desired sum of all estrus mount times; and
   indicating means, including means for indicating that both said first and second conditions have been satisfied.

2. An estrus detector as claimed in claim 1, wherein said indicating means includes means for indicating the time elapsed from satisfaction of both said first and second conditions.

3. An estrus detector as claimed in claim 1, wherein said means for indicating that both said first and second conditions have been satisfied includes a flashing display operable upon satisfaction of both said first and second conditions.

4. An estrus detector as claimed in claim 1, wherein said means for sensing estrus mounts comprises a single sensor, wherein said means for numerically summing and storing sensed estrus mounts and said means for determining and storing the approximate time elapsed during a sensed estrus mount are both arranged to operate in response to each activation of said single sensor.

5. An estrus detector as claimed in claim 1, wherein said processing means is supported in a unitary housing.

6. An estrus detector as claimed in claim 5, wherein said indicating means is supported in said unitary housing.

7. An estrus detector as claimed in claim 5, wherein said processing means is hermetically sealed in said unitary housing.

8. An estrus detector as claimed in claim 1, wherein said processing means is encapsulated in a unitary housing comprising an epoxy resin.

9. An estrus detector as claimed in claim 1, further comprising reset means for resetting simultaneously said means for numerically summing and storing sensed estrus mounts, said means for determining and storing the approximate time elapsed during a sensed estrus mount, and said means for summing the estrus mount times.

10. An estrus detector as claimed in claim 1, wherein said indicating means further includes means for displaying a representation of said programmed desired sum of sensed estrus mounts and said programmed desired sum of all estrus mount times.

11. An estrus detector as claimed in claim 10, wherein said displaying means includes means for displaying a single symbol representing both said programmed desired sums.

12. An estrus detector as claimed in claim 10, further comprising reset means for resetting simultaneously said means for programming a desired sum of sensed estrus mounts, said means for programming a desired sum of all estrus mount times, and said means for displaying a representation of both said programmed sums.

13. An estrus detector as claimed in claim 12, wherein said reset means is includes means to simultaneously reset said means for numerically summing and storing sensed estrus mounts, said means for determining and storing the approximate time elapsed during a sensed estrus mount, and said means for summing the estrus mount times.

* * * * *